United States Patent [19]

Daniels et al.

[11] 4,397,646

[45] Aug. 9, 1983

[54] CONTOURED BABY DIAPER

[75] Inventors: Robert C. Daniels; Florence S. Daniels, both of Piscataway, N.J.

[73] Assignee: Blessings Corp., Middlesex, N.J.

[21] Appl. No.: 247,100

[22] Filed: Mar. 24, 1981

[51] Int. Cl.³ .............................................. A41B 13/02
[52] U.S. Cl. .................................... 604/381; 604/386
[58] Field of Search .............. 128/286, 287, 288, 289, 128/290 H; 604/367, 372, 378, 381, 382, 386, 393-394

[56] References Cited

U.S. PATENT DOCUMENTS 3,063,452 11/1962 Del Guercio ...................... 128/284
3,237,625 3/1966 Johnson ............................. 128/288
3,312,981 4/1967 McGuire et al. .................... 128/288
3,386,443 6/1968 Goldstein ............................ 128/287
3,720,212 3/1973 Kaupin ............................... 128/288
3,828,785 8/1974 Gamm et al. ....................... 128/288
3,838,692 10/1974 Levesque ........................... 128/284
3,882,871 5/1975 Taniguchi ........................... 128/287
4,244,367 1/1981 Rollenhagen ...................... 128/288

Primary Examiner—C. Fred Rosenbaum
Attorney, Agent, or Firm—Hopgood, Calimafde, Kalil, Blaustein & Judlowe

[57] ABSTRACT

This invention is a diaper that is used repeatedly; and is suitable for such use without deterioration after repeated sterilizations in a diaper laundry.

5 Claims, 6 Drawing Figures

U.S. Patent   Aug. 9, 1983   Sheet 1 of 2   4,397,646
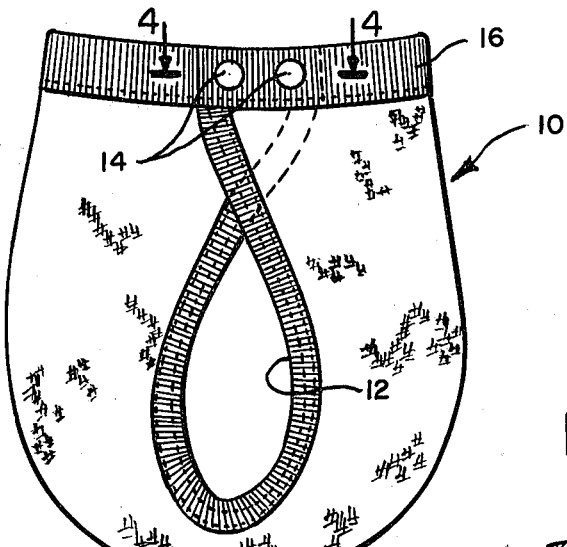
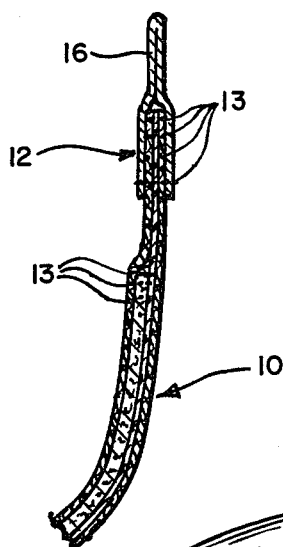
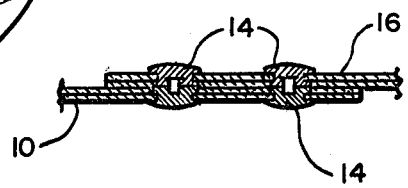
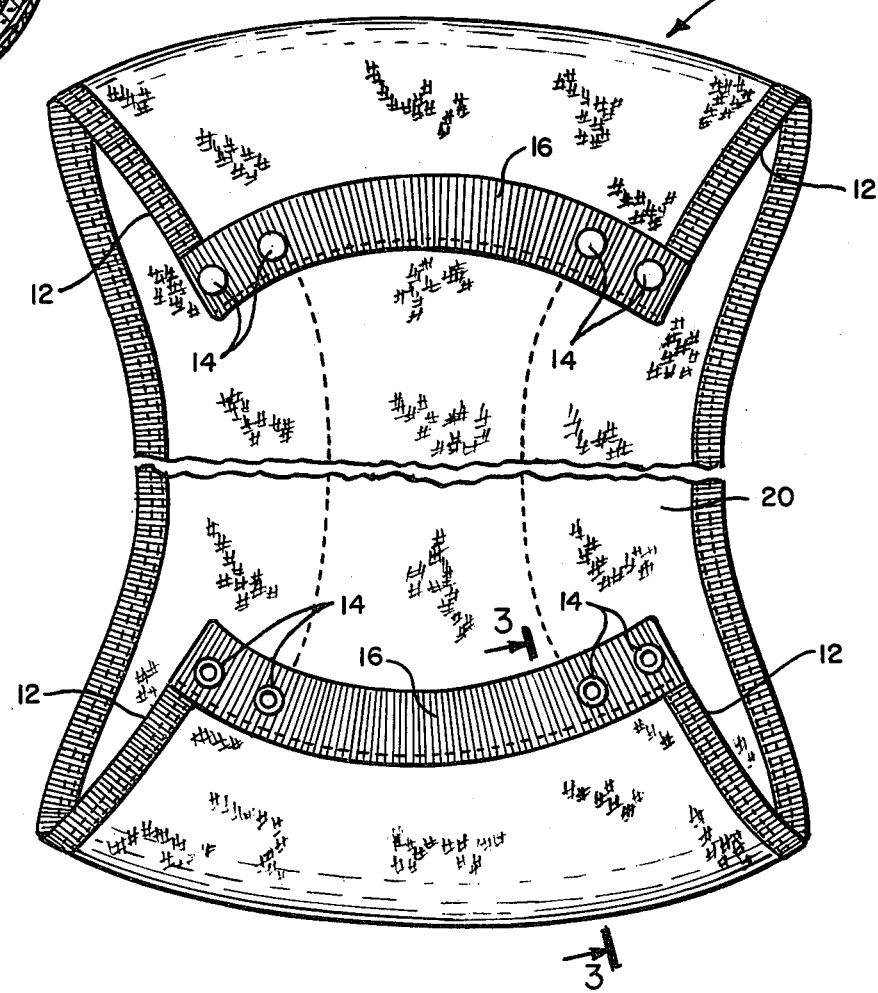

FIG. 5.
FIG. 6.
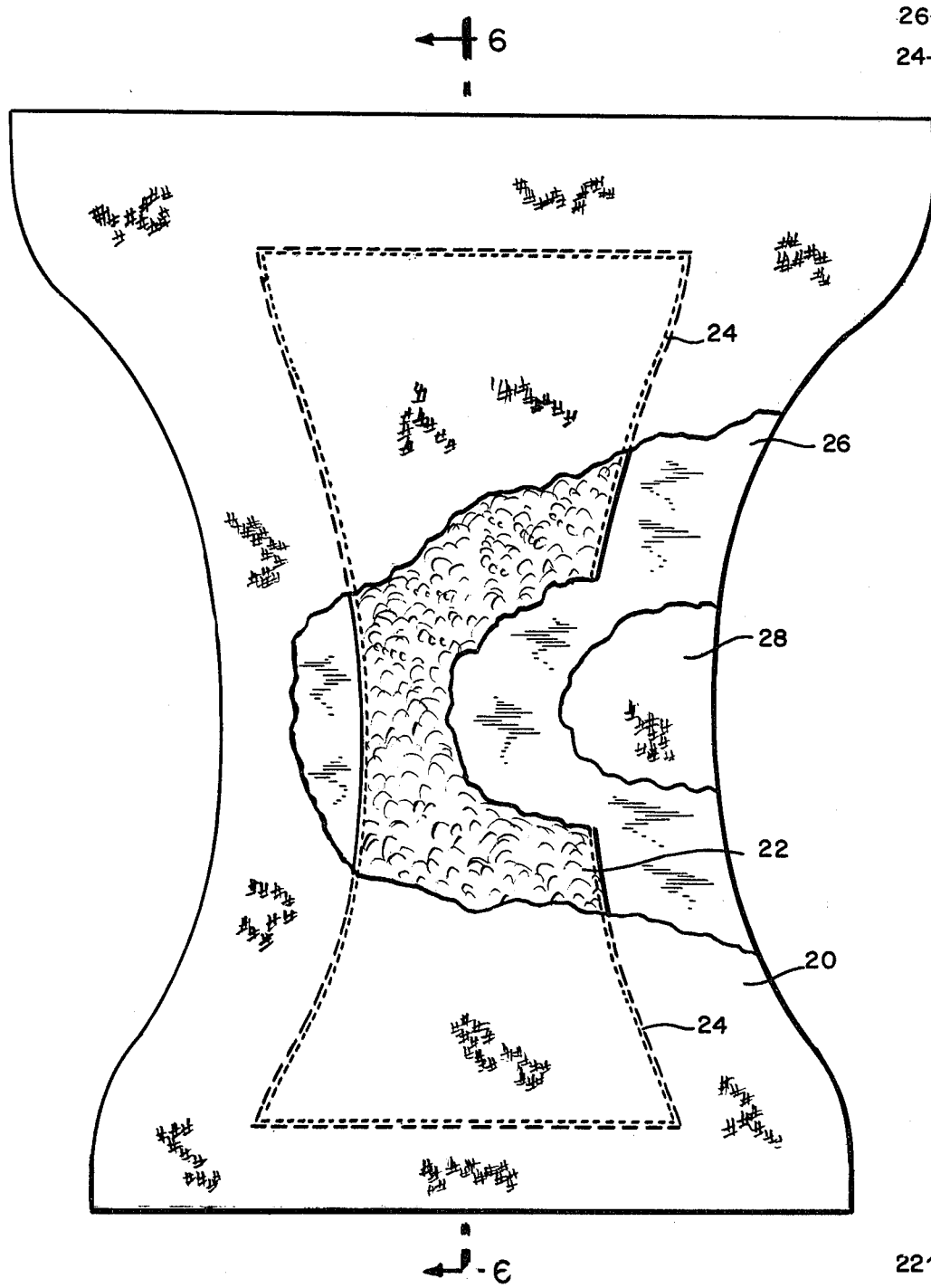
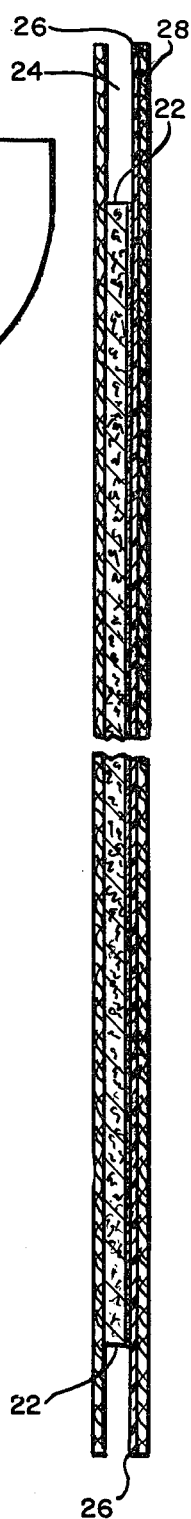

CONTOURED BABY DIAPER

BACKGROUND AMD SUMMARY OF INVENTION

Paper diapers have come into general use and have the convenience that they can be thrown away after each use. Because of the increase in the kind of paper that has to be used for diapers and the substantial increase in the cost of the paper, it has become more economical to make diapers out of cloth that can be laundered after each use and supplied to the customers on a rental basis.

The diapers are made of material that can be laundered after each use and then returned to the customer for repeated use. The construction of the diaper makes it practical to use each diaper repeatedly with sterilization after each use. Because of the durability of the diapers, each one can be used often enough to make the rental services more economical than the use of throwaway paper stock which is made of a combination of sheets that can be used repeatedly and sterilized after each use.

This invention makes use of a combination of sheets and a highly absorbent sheet that is used to prevent wicking and with waterproof layers that combine to produce practical combinations of layers that have different characteristics of absorbency to produce practical porosity for the diapers.

Other objects, features and advantages of the invention will appear or be pointed out as the description proceeds.

BRIEF DESCRIPTION OF DRAWING

In the drawing, forming a part hereof, in which like reference characters indicate corresponding parts in all the views;

FIG. 1 is an assembly view of the diaper of this invention when applied to a child when in use;

FIG. 2 is a view of the diaper of FIG. 1 but with the diaper opened up and ready to put on a child as shown in FIG. 1;

FIG. 3 is an enlarged sectional view taken on the line 3—3 of FIG. 2;

FIG. 4 is an enlarged sectional view taken on the line 4—4 of FIG. 1 and showing the way in which overlapping edges of the diaper are held in place by snap fasteners;

FIG. 5 is a view of the diaper of this invention before ribbing is applied to the periphery of the partially finished diaper shown in FIG. 5; and FIG. 6 is an enlarged sectional view, partly broken away, taken on the line 6—6 of FIG. 5.

DESCRIPTION OF PREFERRED EMBODIMENT

FIG. 1 shows the folded diaper 10 with a leg opening 12 and with the waist portions of the diaper held together by snap fasteners 12 which are secured to the belt. The snap fasteners may be made of any material such as metal or plastic such as nylon.

When the diaper 10 is opened up by releasing the snaps 14, the diaper can be removed from the child's body and occupies a position such as shown in FIG. 2. The snaps 14, when released from one another, permit the belt portions 16 to move apart as shown in FIG. 2 and the child can be lifted from the diaper since the leg openings 12 are no longer closed at the belt of the diaper. The belt 16 is gathered as shown in FIGS. 1 and 2 and the leg openings 12 are also gathered as shown in FIGS. 1 and 2. The gathers 16 and 12 are sewed by stitching which secures the belt 16 and the leg openings 12 to the top and side portions of the leg openings 12.

FIGS. 5 and 6 show the diaper in partially finished position. The diaper is made of layers of material before the gathering at the leg openings 12 and at the belt portions 16. Before there is any gathering at the belt or at the leg openings, all portions of the diaper are flat. Features shown in FIGS. 5 and 6 include a cotton interlock 20 which is the inside face of the diaper and there is a soaker layer 22 which is originally welded to the soaker; and after the layers 20 and 22 have been welded, such as by adhesive, they are sewed together along the lines 24. The soaker layer 22 is made of material which is much narrower than the interlock so that when the diaper is wet, the water is concentrated in the soaker layer 22 which may be several layers thick. Another layer 26 which is of substantially the same area as the cotton interlock 20 and behind the interlock 20 is made of Teflon coated polyester or equivalent material which prevents wetness of the soaker layer 22 passing from the soaker through the outer polyester layer 28. The layer of material 28 to the right of the polyester in FIG. 6 is the outer layer of the diaper when in use.

The gathered material 12 and 16 is stretched to the periphery of the construction shown in FIG. 3 and gathers the sides to give them an elastic edge portion sewed by threads 13. The outer layer is made of polyester.

The preferred embodiment of the invention has been illustrated and described, but changes and modifications can be made and some features can be used without others without departing from the appended claims.

What is claimed is:

1. A cotton fitting diaper comprising flat superimposed layers including top and bottom edges, and concavely curved side edges extending along the mid region of the sides of the diaper to form the leg openings of the diaper when worn said layers including:
   (a) a first inner layer of knit cotton material through which moisture may pass, disposed nearest the wearer;
   (b) a second, soaker layer joined to said first layer, said second layer being constructed of water absorbent material and being sized smaller than said other layers, said second layer being joined to said first layer about its periphery and centered thereon forming a margin around said second layer free from contact with said second layer;
   (c) a third barrier layer of water impervious material, joined to the periphery of said first layer to prevent liquid transfer from said second layer; and
   (d) a fourth layer constructed of knit polyester forming the outer layer of said garment, said fourth layer being joined at the periphery to said first and third layers, said third layer preventing the wicking of liquid from said second layer to said fourth layer so that said fourth layer remains dry.

2. The diaper as claimed in claim 1 further including gatherings disposed about the top, bottom and side edges of the layers of the diaper.

3. The diaper as claimed in claim 2 wherein said top and bottom gatherings include fastening means for fastening said diaper about the body of wearer.

4. The diaper as claimed in claim 2 wherein said gatherings include elastic means for closely fitting said diaper about the wearer.

5. The diaper as claimed in claim 1 wherein said third layer comprises Teflon coated polyester.

* * * * *